US011953387B2

United States Patent
Özer et al.

(10) Patent No.: US 11,953,387 B2
(45) Date of Patent: Apr. 9, 2024

(54) CIRCUITRY FABRICATED ON A FLEXIBLE SUBSTRATE

(71) Applicant: Arm Limited, Cambridge (GB)

(72) Inventors: Emre Özer, Cambridge (GB); Jedrzej Kufel, Cambridge (GB); John Phillip Biggs, Cambridge (GB)

(73) Assignee: Arm Limited, Cambridge (GB)

(*) Notice: Subject to any disclaimer, the term of this patent is extended or adjusted under 35 U.S.C. 154(b) by 65 days.

(21) Appl. No.: 17/648,759

(22) Filed: Jan. 24, 2022

(65) Prior Publication Data

US 2022/0236124 A1 Jul. 28, 2022

(30) Foreign Application Priority Data

Jan. 28, 2021 (GB) .................................... 2101203

(51) Int. Cl.
G01L 1/00 (2006.01)
G01L 1/22 (2006.01)
H05K 1/02 (2006.01)

(52) U.S. Cl.
CPC ............... G01L 1/22 (2013.01); H05K 1/028 (2013.01); *H05K 2201/10151* (2013.01)

(58) Field of Classification Search
CPC . G01L 1/22; H05K 1/028; H05K 2201/10151
See application file for complete search history.

(56) References Cited

U.S. PATENT DOCUMENTS

| 2002/0126005 | A1* | 9/2002 | Hardman | ............ | B60C 23/0493 |
| | | | | | 340/447 |
| 2007/0205791 | A1* | 9/2007 | Ahmad | .............. | G01R 31/2817 |
| | | | | | 73/862.474 |

(Continued)

FOREIGN PATENT DOCUMENTS

| EP | 2315101 A1 | 4/2011 |
| EP | 3695778 A1 | 8/2020 |
| GB | 2586526 A | 2/2021 |

OTHER PUBLICATIONS

Takei, et al., "Highly sensitive electronic whiskers based on patterned carbon nanotube and silver nanoparticle composite films", Department of Electrical Engineering and Computer Science, and Berkeley Sensor and Actuator Center, University of California, Berkeley, CA 94720, Dec. 18, 2013.

(Continued)

*Primary Examiner* — Max H Noori
(74) *Attorney, Agent, or Firm* — NIXON & VANDERHYE P.C.

(57) ABSTRACT

Apparatuses and methods of operating apparatuses are disclosed. An apparatus comprises a flexible substrate and circuitry fabricated on the flexible substrate to perform data processing. At least one strain detector generates a strain signal which is dependent on a flexing state of the strain detector on the flexible substrate. A strain history control unit samples the at least one strain signal from the at least one strain detector at a plurality of time points and records a strain snapshot at each time point comprising data dependent on the at least one strain signal from the at least one strain detector. The data processing performed by the circuitry is dependent on the plurality of strain snapshots recorded.

20 Claims, 8 Drawing Sheets

(56) References Cited

U.S. PATENT DOCUMENTS

| | | | |
|---|---|---|---|
| 2011/0247863 A1* | 10/2011 | Watanabe | H05K 1/028 |
| | | | 29/829 |
| 2015/0296622 A1 | 10/2015 | Jiang et al. | |
| 2016/0050750 A1* | 2/2016 | Rogers | H05K 3/285 |
| | | | 361/767 |
| 2017/0176167 A1 | 6/2017 | Keller et al. | |
| 2018/0146545 A1* | 5/2018 | Wang | H05K 1/028 |
| 2019/0257704 A1 | 8/2019 | Steyn | |
| 2021/0112657 A1* | 4/2021 | Edmundson | H05K 1/028 |
| 2021/0318191 A1* | 10/2021 | Okulov | G01M 5/0041 |
| 2023/0136688 A1* | 5/2023 | Leerentveld | G09G 3/3233 |
| | | | 345/207 |

OTHER PUBLICATIONS

Petti, et al., "Metal oxide semiconductor thin-film transistors for flexible electronics", (2016) Metal oxide semiconductor thin-film transistors for flexible electronics. Applied Physics Reviews, 3 (2). 021303. ISSN 1931-9401, http://sro.sussex.ac.uk/id/eprint/61869/.
Zumeit, et al., "Nanoribbon-Based Flexible High-Performance Transistors Fabricated at Room Temperature", James Watt School of Engineering University of Glasgow G12 8QQ Glasgow, UK, 2020, https://doi.org/10.1002aelm.201901023.

* cited by examiner

CIRCUITRY FABRICATED ON A FLEXIBLE SUBSTRATE

CROSS-REFERENCE TO RELATED APPLICATIONS

This application claims priority pursuant to 35 U.S.C. 119(a) to United Kingdom Patent Application No. 2101023.4, filed Jan. 28, 2021, which application is incorporated herein by reference in its entirety.

FIELD OF THE INVENTION

The present techniques relate to circuitry fabricated on the flexible substrate.

BACKGROUND

Whilst in the past circuitry has been almost exclusively fabricated on a crystalline silicon substrate, more recently progress has been made in the fabrication of circuitry on other substrates, some of which may not be as rigid as crystalline silicon.

SUMMARY

At least some examples provide an apparatus comprising:
a flexible substrate; and
circuitry fabricated on the flexible substrate to perform data processing, wherein the circuitry comprises:
  at least one strain detector arranged to generate a strain signal which is dependent on a flexing state of the strain detector on the flexible substrate; and
  a strain history control unit arranged to sample the at least one strain signal from the at least one strain detector at a plurality of time points and to record a strain snapshot at each time point comprising data dependent on the at least one strain signal from the at least one strain detector,
wherein data processing performed by the circuitry is dependent on the plurality of strain snapshots recorded.

At least some examples provide a method of operating an apparatus, wherein the apparatus comprises a flexible substrate and circuitry fabricated on the flexible substrate to perform data processing, the circuitry comprising at least one strain detector, the method comprising:
  generating a strain signal in the at least one strain detector which is dependent on a flexing state of the strain detector on the flexible substrate;
  sampling the at least one strain signal from the at least one strain detector at a plurality of time points;
  recording a strain snapshot at each time point comprising data dependent on the at least one strain signal from the at least one strain detector; and
  controlling data processing performed by the circuitry in dependence on the plurality of strain snapshots recorded.

At least some examples provide an apparatus comprising:
a flexible substrate;
circuitry fabricated on the flexible substrate to perform data processing;
at least one means for generating a strain signal which is dependent on a flexing state of the flexible substrate;
means for sampling the strain signal from the at least one strain detector at a plurality of time points;
means for recording a strain snapshot at each time point comprising data dependent on the at least one strain signal; and
means for controlling data processing performed by the circuitry in dependence on the plurality of strain snapshots recorded.

BRIEF DESCRIPTION OF THE DRAWINGS

The present techniques will be described further, by way of example only, with reference to embodiments thereof as illustrated in the accompanying drawings, to be read in conjunction with the following description, in which.

DETAILED DESCRIPTION

Figure 1:
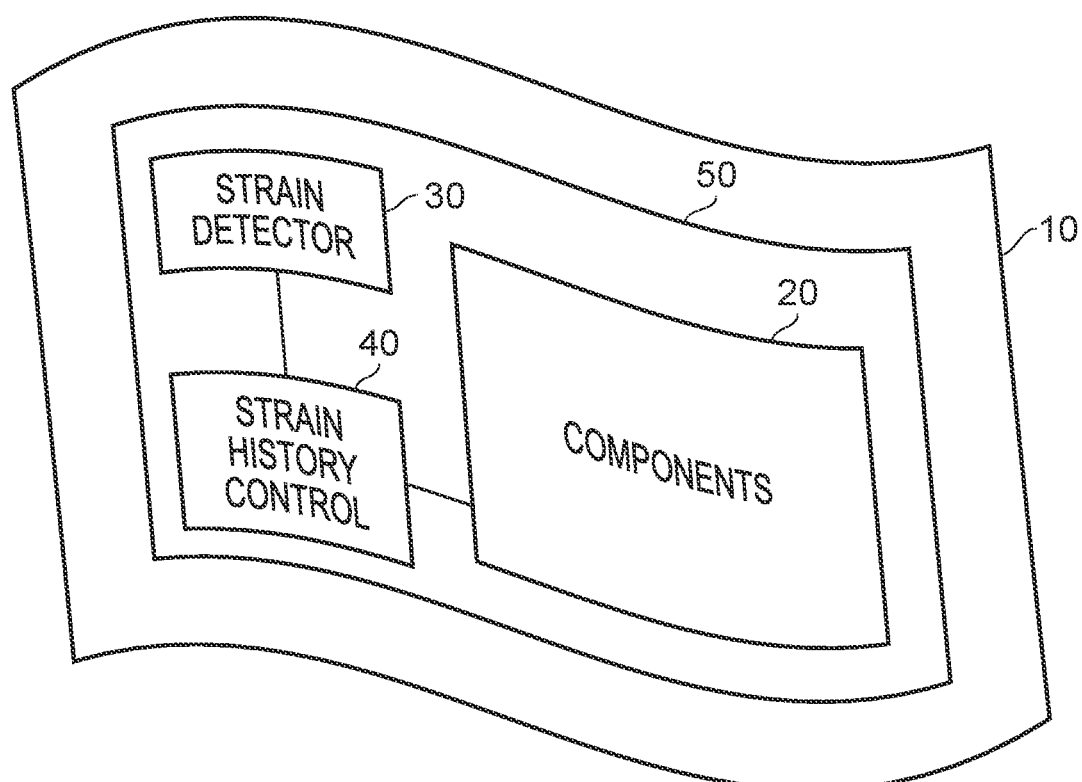
FIG. 1 schematically illustrates circuitry fabricated on a flexible substrate in accordance with some embodiments.

In one example herein there is an apparatus comprising:
a flexible substrate; and
circuitry fabricated on the flexible substrate to perform data processing, wherein the circuitry comprises:
  at least one strain detector arranged to generate a strain signal which is dependent on a flexing state of the strain detector on the flexible substrate; and
  a strain history control unit arranged to sample the at least one strain signal from the at least one strain detector at a plurality of time points and to record a strain snapshot at each time point comprising data dependent on the at least one strain signal from the at least one strain detector,
wherein data processing performed by the circuitry is dependent on the plurality of strain snapshots recorded.

The present techniques are based on the recognition that circuitry fabricated on a flexible substrate (e.g. on plastic, on polymer, on cellulose, or any other such flexible substrate) will operate under mechanical stress or strain, e.g. tensile strain when the substrate is stretched and compressive strain when the substrate is compressed. Such tension and compression may for example result from flexing of the substrate, where a given flexed configuration may put one surface of the substrate in tension whilst putting the opposite surface of the substrate in compression. Whilst a certain degree of flexing of such substrates is tolerable, as long as the substrate material and the circuitry components remain within their elastic regions, the present techniques however note that the performance parameters of circuitry components change under such stress or strain. For example under tensile strain, i.e. when stretched, the charge mobility of metal oxide thin-film transistors (TFTs), in particular indium gallium zinc oxide (IGZO) TFTs, increases when the threshold voltage decreases and therefore the gate delay becomes smaller. Conversely under compressive strain (i.e. when compressed) the opposite effect is observed. Generally when the substrate returns to a flat configuration the device parameters will also recover to their original values. A similar behaviour is also observed in silicon-based nanoribbon TFTs. In this case the parameter shift is found to be caused by a change the electronic band structure. However long or repeated strain cycles (e.g. an ongoing sequence of the substrate being flat—in tension—flat—in tension—flat etc.) will typically lead to performance degradation of the device parameters and may even lead to device failure.

In this context the present techniques propose that an apparatus comprising a flexible substrate and circuitry fabricated on the flexible substrate is augmented by the addition of at least one strain detector which is sensitive to the current flexing state of the substrate. A strain signal generated by the strain detector is sampled by a control unit forming part of the circuitry in order to record a "strain snapshot", i.e. an indication of the strain state of the substrate at a given moment in time. Multiple strain snapshots are thereby recorded and the data processing performed by the circuitry fabricated from flexible substrate is influenced on the basis of these snapshots. The variation in the data processing performed may take a wide variety of forms, from a minor modification such as the recording of a derivate data item or the generation of an associated signal to a major modification such as powering down some or even all components.

The strain signal generated by the at least one strain detector may be made use of in a variety of ways and thus the data dependent on the at least one strain signal may take various forms. However in some embodiments this comprises a strain indication taken from a finite set of discrete strain states which may facilitate efficient storage of the strain snapshot generated at each time point. Accordingly in some embodiments the data dependent on the at least one strain signal from the at least one strain detector recorded by the strain history control unit comprises a strain indication dependent on the at least one strain signal, wherein the strain indication is taken from a finite set of discrete strain states, and wherein the finite set of discrete strain states comprise an unstrained state and at least one strained state. Thus in a minimal configuration the finite set of discrete strain states may be binary, comprising the unstrained (flat) state and a strained state. In such a case the strained state may be generic (i.e. covering either tension or compression) or may correspond to a particular one of either tension or compression. Nevertheless at least one strained state, i.e. possibly more than one strain state, is contemplated and for example the finite set of discrete strain states may correspond to three possible states, namely unstrained (flat), in tension, and in compression. Thus in some embodiments the at least one strained state comprises an in-tension state and an in-compression state.

The strain indications received from all strain detectors which are provided may be handled in a variety of ways, in particular either individually or collectively. Accordingly in some embodiments the strain history control unit is arranged to record the strain indication for each strain detector. Equally, in some embodiments the strain history control unit is arranged to record the strain indication as a summary strain indication for all strain detectors.

A summary strain indication may be generated in a variety of ways but according to some embodiments the strain history control unit is arranged to determine the summary strain indication by majority vote of strain indications of each strain detector.

In some embodiments the strain history control unit is arranged to record the strain snapshot at each time point further comprising location information of the at least one strain detector. This may for example indicate a relative position of the strain detector on the substrate or it may indicate a component of the circuitry with which the strain detector is associated.

The strain history control unit may record the strain snapshots in a variety of ways, but in some embodiments the apparatus further comprises a strain history storage, wherein the strain history control unit is arranged to record the strain snapshot at each time point in the strain history storage.

The strain history control unit may be configured in a variety of ways and different embodiments may have a range of data processing ability. For example the strain history control unit may be configured as a simple component which only records the snapshots but does no more with them, whereas in other embodiments the strain history control unit may be provided with further data processing ability in order to derive useful derivative data from the snapshots recorded. In some embodiments the circuitry comprises a data processing unit, and wherein the data processing unit has access to the strain history storage and wherein the data processing unit is arranged to control the data processing performed by the circuitry in dependence on the plurality of strain snapshots recorded. For example this data processing unit may be a significant component which is provided by the apparatus embodied on the flexible substrate and a minor task which it carries out (in addition to its usual data processing operations) may be to access the strain history storage in order to monitor the history of flexing to which the substrate has been subjected.

Alternatively or in addition the circuitry may further be provided with a strain predictor which monitors the strain snapshots recorded and on the basis thereof is able to predict future flexing of the substrate. Useful modification of the data processing operations of the circuitry can then be implemented. Thus in some embodiments the circuitry comprises a strain predictor, wherein the strain predictor has access to the strain history storage and wherein the strain predictor is arranged to generate a strain prediction indicative of a predicted period of flexing of the flexible substrate in dependence on the plurality of strain snapshots recorded. To take just one illustrative example consider the situation in which the flexible substrate is embedded in clothing worn by a person, who has periods during the day when they are significantly physically active (thus causing the substrate to flex), whilst having other periods when they barely move. Assuming that there is flexibility in the timing of when the data processing operations are performed by the circuitry, it may be advantageous for these to be timed to coincide with the periods of physical inactivity in order to prolong the lifetime of the apparatus.

A modification of the data processing operations of the circuitry in dependence on the strain prediction may take a wide variety of forms, but in some embodiments the circuitry is responsive to the strain prediction indicative of the predicted period of flexing to enter a reduced activity mode for the predicted period, wherein the reduced activity mode comprises at least one of:
  at least some components of the circuitry being in a low power state;
  at least some components of the circuitry being provided with a reduced frequency clock signal; and
  at least some components of the circuitry being powered off.

In some embodiments the data processing performed by the circuitry comprises generation of an ageing prediction for the apparatus, wherein the ageing prediction is dependent on the plurality of strain snapshots recorded. Such an ageing prediction may take a variety of forms either internal to the device or as a signal to the user of the device. For example in the latter case the ageing prediction could be a signal to the user indicating that the apparatus predicts that it will only be reliably operational for a further limited period.

Where it is recognised that a flexed state of the substrate may cause a variation in signal propagation speeds within the circuitry, the present techniques propose that the apparatus is configured such that a clock frequency at which the circuitry operates takes into account the retardation of the signals when the substrate is flexed. Accordingly in some embodiments the at least one strain detector is arranged to operate at a clock speed defined when the flexing state of the at least one strain detector on the flexible substrate is an in-compression state. For example in the case of IGZO and silicon-based nanoribbon (two TFT technologies) compressive gate delays may define the relevant slowest needed clock speed.

Alternatively it is further recognised that the substrate may be formed out of materials where the phenomenon is inverted, i.e. that the slowest propagation speeds result from a tensile state, and accordingly in some embodiments the at least one strain detector is arranged to operate at a clock speed defined when the flexing state of the at least one strain detector on the flexible substrate is comprises an in-tension state.

When a plurality of strain detectors is provided, these may be distributed in a variety of ways across the flexible substrate. For example in some embodiments the circuitry comprises a plurality of strain detectors randomly distributed across the flexible substrate. In other embodiments the circuitry comprises a plurality of strain detectors distributed in a regular pattern across the flexible substrate. In some embodiments the circuitry comprises a plurality of strain detectors distributed across the flexible substrate, wherein each strain detector is positioned in association with a component of the circuitry.

The circuitry fabricated on the flexible substrate may take a variety of forms, but in some embodiments the circuitry fabricated on the flexible substrate comprises a flexible system-on-chip, wherein the strain signal generated by the strain detector on the flexible substrate is indicative of a flexing state of the flexible system-on-chip.

In one example herein there is a method of operating an apparatus, wherein the apparatus comprises circuitry fabricated on the flexible substrate to perform data processing, the circuitry comprising at least one strain detector, the method comprising:
  generating a strain signal in the at least one strain detector which is dependent on a flexing state of the strain detector on the flexible substrate;
  sampling the at least one strain signal from the at least one strain detector at a plurality of time points;
  recording a strain snapshot at each time point comprising data dependent on the at least one strain signal from the at least one strain detector; and
  controlling data processing performed by the circuitry in dependence on the plurality of strain snapshots recorded.

In one example herein there is an apparatus comprising:
  a flexible substrate;
  circuitry fabricated on the flexible substrate to perform data processing;
  at least one means for generating a strain signal which is dependent on a flexing state of the flexible substrate;
  means for sampling the strain signal from the at least one strain detector at a plurality of time points;
  means for recording a strain snapshot at each time point comprising data dependent on the at least one strain signal; and
  means for controlling data processing performed by the circuitry in dependence on the plurality of strain snapshots recorded.

Some particular embodiments are now described with reference to the figures.

FIG. 1 schematically illustrates an apparatus in accordance with some embodiments, wherein a flexible material 10 provides a substrate upon which various items of circuitry 50 are fabricated. The flexible material 10 may be any material onto which further conducting, semi-conducting, and/or insulating items may be deposited in order to form such circuitry. Possibilities such as plastic, polymer, and cellulose are given here merely by way of example. The circuitry 50 may comprise only very few components or a great number, although according to the present techniques the components comprise at least one strain detector 30 and a strain history control unit 40. Generically, further components of the circuitry 20 are also shown. In operation the strain detector 30 is arranged to generate a strain signal which depends on a current flexing state of the strain detector 30 on the flexible substrate 10. The strain signal is sampled by strain history control unit 40, on the basis of which it records a strain snapshot which comprises data dependent on the strain signal. The strain history control unit 40 records multiple such strain snapshots and these strain snapshots affect the data processing operations performed by the components of the circuitry 50. The strain monitoring functionality provided by the strain detector 30 and the strain history control unit 40 notwithstanding, the data processing operations performed by the circuitry 50 can take a huge range of forms and the present techniques are not limited to any particular operation, purpose, or use of the circuitry. Nevertheless this strain monitoring functionality implemented in association with a flexible substrate 10 may be of particular applicability in embodiments in which are expected to be subject to a degree of flexing, whether acute or chronic.

Figure 2A:
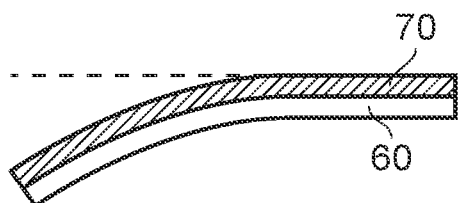
FIGS. 2A and 2B schematically illustrates two flexed states of a flexible substrate in accordance with some embodiments.
Figure 2B:
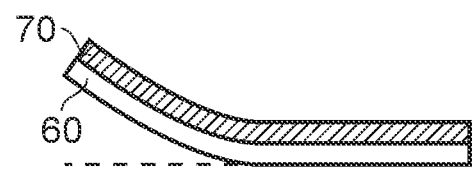
Figure 2C:
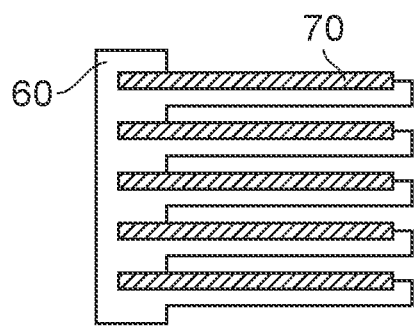
FIG. 2C schematically illustrates a set of e-whisker printed strain sensors in accordance with some embodiments.

FIGS. 2A, 2B, and 2C schematically illustrate various aspects of some strain detectors in accordance with some embodiments. These strain detectors are formed from printed composite nanomaterial, which is viewed in a side view in FIGS. 2A and 2B, thus showing a (nominally) lower material 60 and a (nominally) upper material 70, where the material 60 also forms the substrate forming the flexible base on which circuitry (including the strain detectors) is laid down. These may for example be printed strain sensors based on carbon nanotube (CNT) paste and silver nanoparticles printed on a polymer such as polydimethylsiloxane (PDMS). The material 70 thus forms the functional component of the strain detectors, in particular being selected such that its resistance varies with the tensile or compressive strain to which the substrate is subjected. In FIG. 2A it can be seen that the strain detector layer 70 is in tension, being bent downwards together with the substrate 60. Conversely in FIG. 2B can be seen that the strain detector layer is in compression, being bent upwards together with the substrate 60. FIG. 2C shows a configuration in which multiple strain detectors (also known as "e-whiskers") are arranged parallel to one another on a common portion of substrate material. Hence in any of these examples monitoring the current flowing through the strain detector allows a determination to be made of whether the detector is currently in tension or in compression (or neither).

Figure 3A:
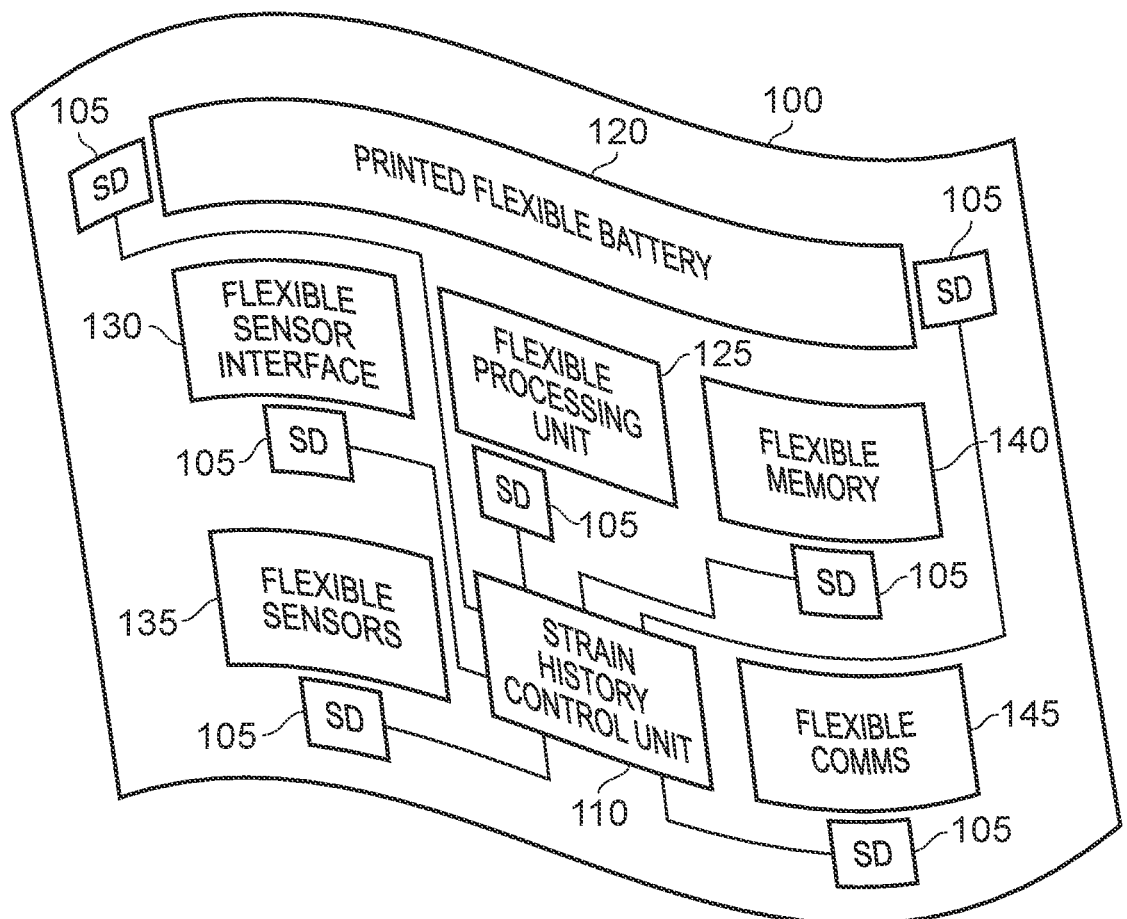
FIG. 3A schematically illustrates circuitry fabricated on a flexible substrate in accordance with some embodiments.

FIG. 3A schematically illustrates an apparatus comprising a flexible substrate 100 in accordance with some embodiments. The comments made above with respect to FIG. 1 equally apply to this illustrated embodiment. The flexible substrate 100 may be termed a flexible printed circuit board (PCB). The resulting apparatus is shown to comprise a strain history control unit 110 with multiple strain detectors (SD) 105 each connected to the strain history control unit 110. Specific examples of further components of the circuitry provided on the flexible substrate 100 are also shown in FIG. 3A, namely printed flexible battery 120, flexible processing unit 125, flexible sensor interface 130, flexible sensors 135, flexible memory 140, and flexible communications unit 145. Only the connections between the strain detectors 105 and the strain history control unit 110 are explicitly shown in FIG. 3A, merely for clarity of illustration. Having a processing unit 125, a memory 140, a battery 120, and a communications unit 145 the apparatus of FIG. 3A, the apparatus may be configured to perform a great variety of data processing operations, in particular with respect to data which is derived from the flexible sensors 135 (via the flexible sensor interface 130). To take just one example the apparatus may be arranged to periodically communicate information about its surroundings detected by sensors to a remote further data processing apparatus, likely one with greater data processing and storage capability. One of the advantages of a flexible substrate is its suitability for incorporation into clothing or other worn items and as such the data gathered by the sensors may relate to the user wearing the item which includes the apparatus on a flexible substrate. Such data may relate to personal comfort, health, fitness, and so on.

Figure 3B:
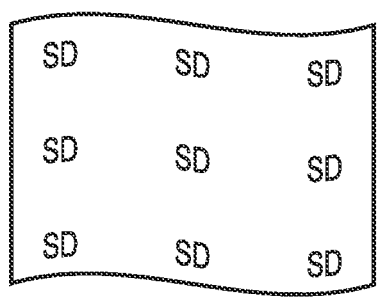
FIGS. 3B and 3C schematically illustrates example distributions of strain detectors on a flexible substrate in accordance with some embodiments.
Figure 3C:
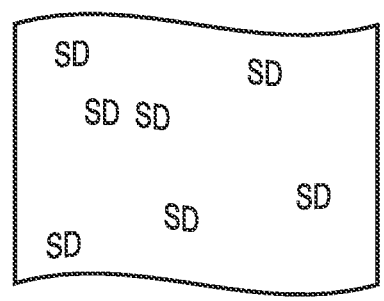

The functionality of the apparatus 100 is further augmented by the provision of the strain detectors (SDs) 105 and the strain history control unit 110, enabling the apparatus to monitor the flexing of the substrate on which it is fabricated and to modify its data processing operations in response as appropriate. As can be seen in the example illustration of FIG. 3A, generally the strain detectors 105 are each arranged to be positioned next to a component of the circuitry. One strain detector lies centrally between the flexible processing unit 125 and strain history control unit 110. Further, a strain detector is located at each end of the printed flexible battery 120. This configuration may be selected because of the proximity of each of the strain detectors to a component of the circuitry. In some examples the strain history control unit, when recording the strain snapshots, also records an indication of the location of the origin of a given strain signal. This information can subsequently be made use of, for example if there is a data indicating that a certain portion of the substrate (where one or more components is/are located) has been subjected to a greater degree of flexing than other areas of the substrate, potentially making the components in that locality more susceptible to damage or ageing. However the strain detectors may also be distributed on the substrate in other manners. FIG. 3B schematically illustrates a substrate on which nine strain detectors (SD) are arranged in a regular grid-like pattern and FIG. 3C schematically illustrates a substrate on which seven strain detectors have been randomly distributed. For example embodiments in which the strain signals from the respective strain detectors are combined in some manner (e.g. by majority voting) to form a single data point as the strain snapshot, the particular distribution of the strain detectors across the substrate may matter less as long as the substrate is generally fully covered. A systematic distribution of the strain detectors may facilitate manufacture.

Figure 3D:
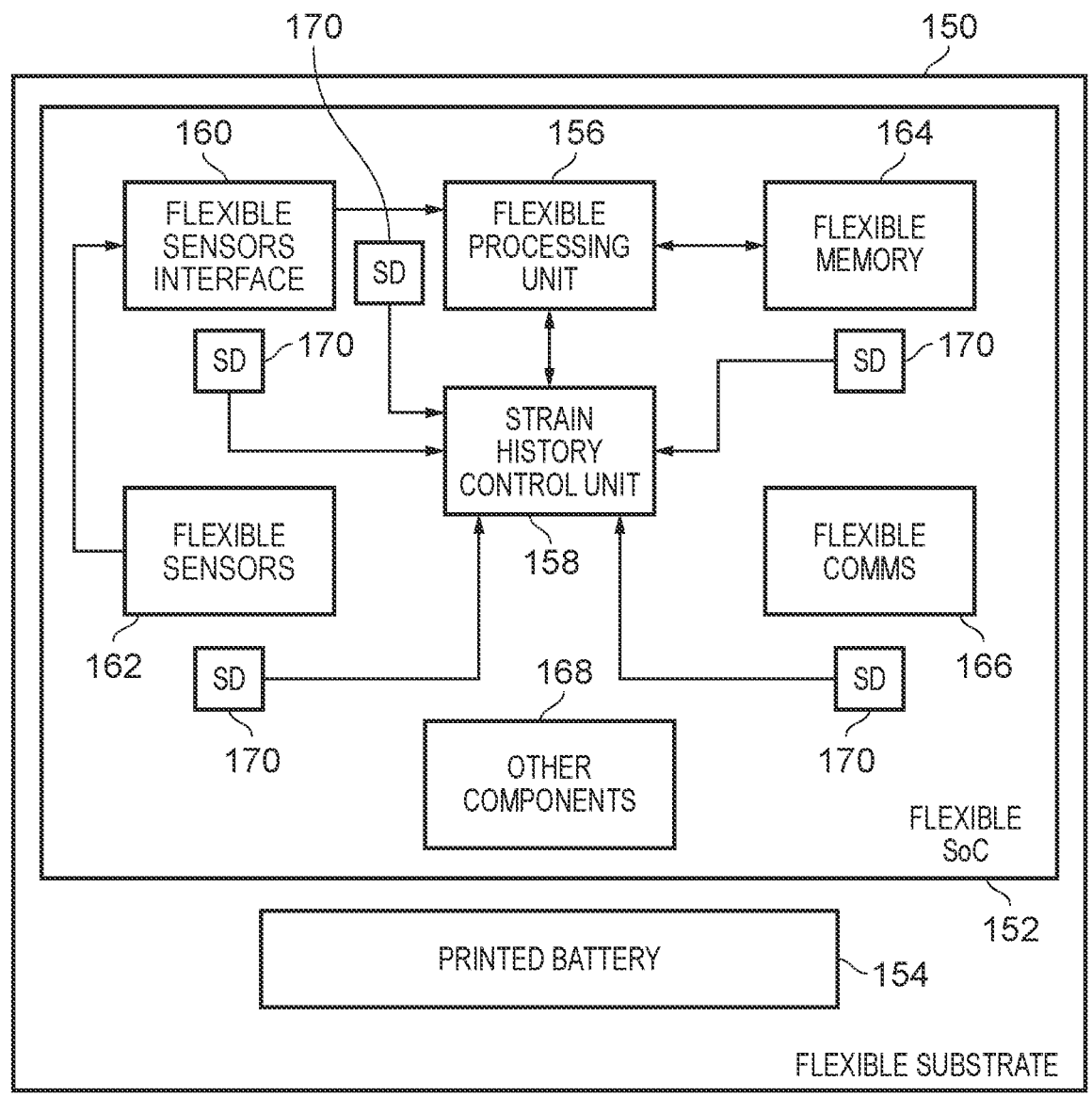
FIG. 3D schematically illustrates circuitry fabricated on a flexible substrate in accordance with some embodiments.

FIG. 3D shows a variant on the embodiment shown in FIG. 3A, schematically illustrating an apparatus comprising a flexible substrate 150 in accordance with some embodiments. The flexible substrate 150 forms the base for a flexible system-on-chip (SoC) 152 and a printed battery 154. As in the example of FIG. 3A, there are various system components shown and SoC 152 comprises flexible processing unit 156, flexible sensor interface 160, flexible sensors 162, flexible memory 164, and flexible communications unit 166. A strain detector (SD) 170 is positioned next to each of these components. Generically shown, further components 168 may form part of the SoC 152 which do not have an associated strain detector. A flexible (printed) battery 154 is also fabricated on the flexible substrate 150, which powers the flexible SoC 152.

Figure 4:
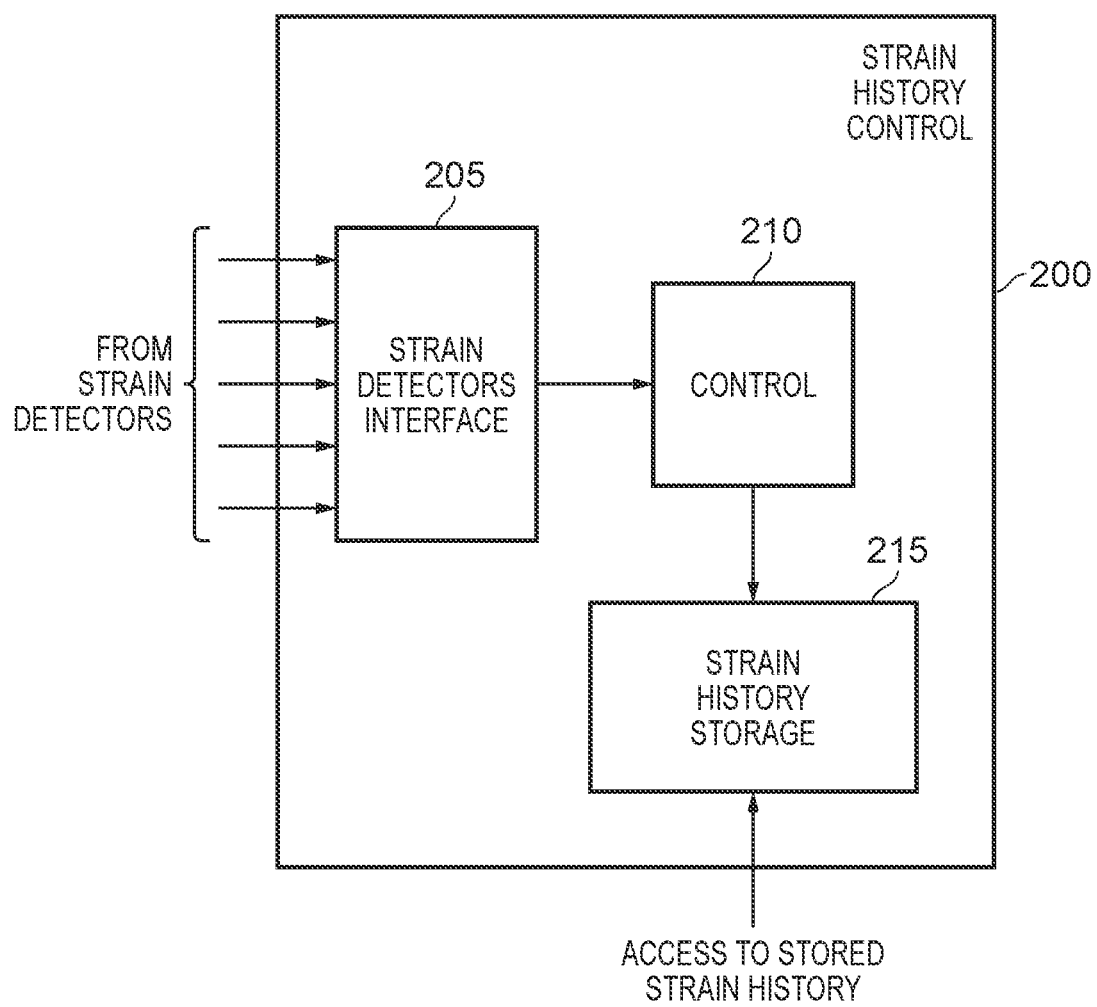
FIG. 4 schematically illustrates a strain history control unit in accordance with some embodiments.

FIG. 4 schematically illustrates the configuration of a strain history control unit 200 in accordance with some embodiments. The strain history control unit 200 is shown to comprise a strain detectors interface 205, the control unit 210, and strain history storage 215. As will be discussed in more detail with respect to FIGS. 5A and 5B, the strain detectors interface 205 may generate status data for each of the respective strain detectors in variety of ways, although a simple representation, such as a binary "flat/planar" or "strained", or a ternary "flat/planar", "tensile" or "compressive" may be used to provide a compact, efficient representation. The strain status data provided by the strain detectors is temporarily held in the strain detectors interface 205 whilst the control unit 210 processes this data to generate a strain snapshot to store in the strain history storage 215. This processing of the strain data input to generate a strain snapshot is periodic, wherein the particular period between the generation of the snapshots is fully implementation dependent, i.e. in some embodiments this may be frequently performed (when a detailed picture of the flexing of the substrate over a short period of time is required), whilst in other embodiments this may be only relatively infrequent (when only a longer-term picture of the flexing of the substrate is needed). Individual data points from each strain detector may form part of the snapshot stored or these may be combined into a single data point representing the overall current strain status of the system. When multiple strain signals are combined into a single data point note that strain indications from the strain detectors may differ from one another, i.e. some locations on the substrate can be in tension, whilst others are flat or in compression. In such cases the control unit 210 may implement any one of a number of different possible algorithms for their combination. In a simple case the overall strain indication may be determined by majority voting. The strain history storage 215 may be provided in various ways. SRAM or non-volatile memory are each possibilities.

Figure 5A:
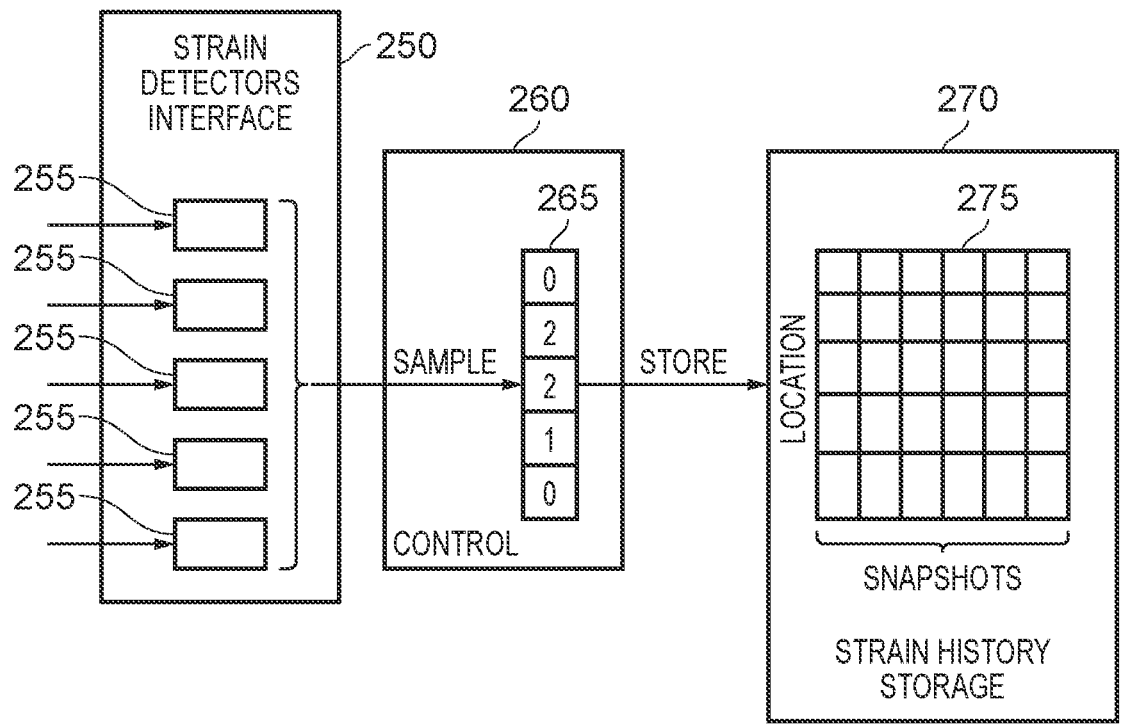
FIG. 5A schematically illustrates the storage of strain snapshots in accordance with some embodiments.
Figure 5B:
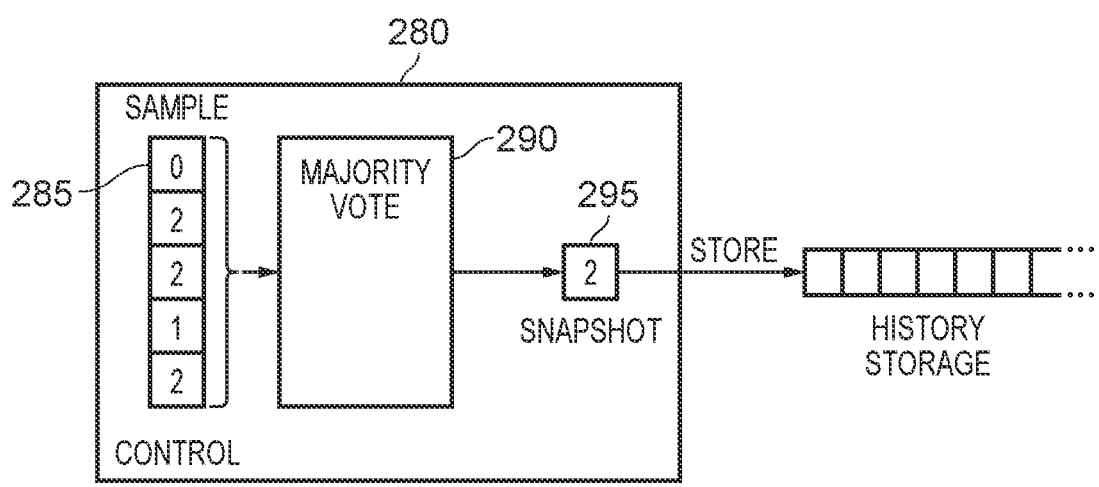
FIG. 5B schematically illustrates the storage of strain snapshots in accordance with some embodiments.

FIGS. 5A and 5B schematically illustrate how the processing of strain signals received from the strain detectors in order to generate the strain snapshots which are stored is performed in two example embodiments. In the example of FIG. 5A the strain signals received from the respective strain detectors are temporarily held in buffers 255 within the strain detectors interface 250. The control unit 260 accesses these buffers in order to sample their content at a selected moment in time, providing a snapshot 265. As can be seen in the example values given in the illustration of FIG. 5A, the signals from the respective strain detectors are represented in a ternary format, i.e. one in which three values are possible, namely 0 (meaning that the corresponding strain detector is "flat"), 1 (meaning that the corresponding strain detector is "in tension"), and 2 (meaning that the corresponding strain detector is "in compression"). Of course these particular meaning of each value are arbitrarily chosen. The particular manner in which the control unit 260 converts the respective strain signals into these values may take various forms, but for example variations in the resistance of each strain detector (due to their current physical flexing state) may be observed by a variation in the voltage levels observed in the buffered signals 255 in the strain detectors interface 250, and the control unit 260 may set corresponding voltage thresholds to categorise the signals into one of the three ternary possibilities. As mentioned above, a ternary configuration is not essential, and for example other embodiments may be provided on the basis of binary categorisation of strain signals, such as "flexed" and "not flexed". Equally, embodiments with more than three categories are also contemplated, where the control unit may then categorise the signals for example as ranging through: strongly in tension; weakly in tension; flat/planar; weakly in compression; and strongly in compression. The snapshot 265 generated by the control unit 260 is then caused to be stored in the strain history storage 270, which over a period of time stores a series of snapshots corresponding to the respective time point at which they were taken. Note that in this embodiment the values corresponding to each individual strain detector are preserved and thus correspond to location information within each snapshot (see 275).

FIG. 5B schematically illustrates a variant on the manner in which the strain snapshots may be created and stored. Here the control unit 280 samples the strain signals in a similar manner to that described above with reference to FIG. 5A, in order to generate a sample 285. However having done so this then forms the input to majority voting circuitry 290, which determines a single value (again in the ternary representation used in the example of FIG. 5A) representative of the whole sample. Here that single value 295 then forms the snapshot which is caused to be stored in the history storage. Accordingly in the example of FIG. 5B the distinction between the strain states observed for each strain detector is not preserved and instead an overall flexing state for the monitored apparatus is stored for each snapshot.

Figure 6:
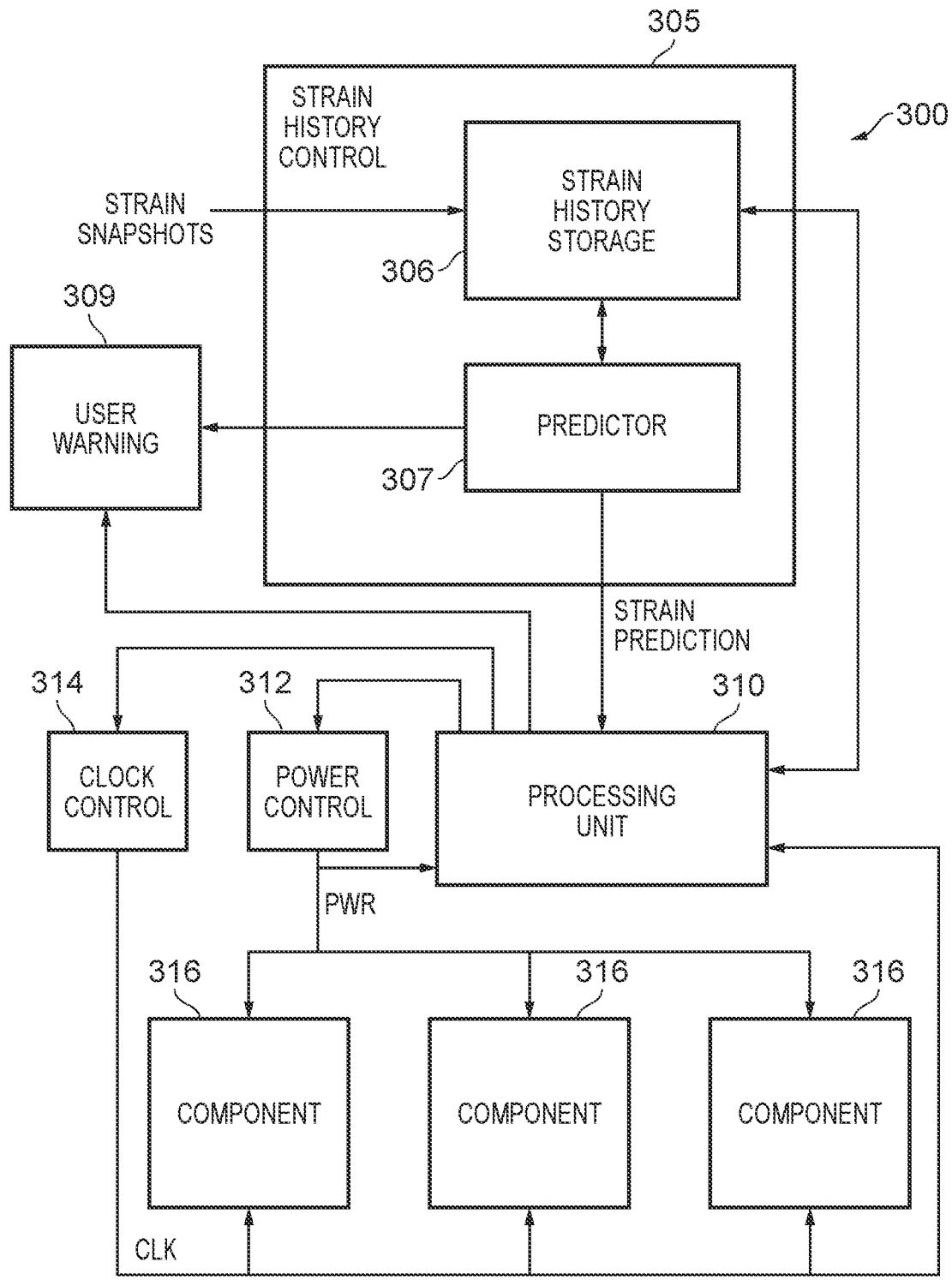
FIG. 6 schematically illustrates various example components of circuitry fabricated on a flexible substrate in accordance with some embodiments.

FIG. 6 schematically illustrates an apparatus according to some embodiments. A strain history control unit 305 is provided which may be configured in accordance with any of the above described embodiments, such that strain snapshots are stored in the strain history storage 306. In this embodiment the strain history control 305 is further provided with a predictor 307, which is arranged to generate a strain prediction on the basis of the snapshots stored in the strain history storage 306. The generation of this strain prediction may take a variety of forms. In one example this may comprise the prediction of an upcoming strain "event", based on the past history of observed flexing of the substrate. For example, where there is a regular temporal pattern of flexing, the predictor may be configured to extrapolate that pattern to indicate when such flexing is expected to occur again. The example of FIG. 6 illustrates that the predictor 307 may itself generate the signal which can trigger a user warning 309 on the basis of such prediction or the strain prediction may be passed to a processing unit 310 to make further use of. The predictor 307 may (for example in combination with the user warning 309) provide sufficient response to the strain snapshots stored and some embodiments may not require the strain prediction to also be passed to the processing unit 310. This warning may be designed to cause the user to take certain remedial action. In one example the warning may be an ageing warning, where the history of flexing is now such that the apparatus should warn the user that it should be replaced before it becomes unreliable or even fails due to flexing-induced degradation.

However the flexibility inherent in the data processing capability of the processing unit 310 means that the response of the apparatus to the strain snapshots stored may instead (or also) derive from the processing unit 310. Indeed the processing unit 310 (as shown) can itself have access to the strain history storage 306, in order to make direct use of the data stored therein. As an example of one such response the processing unit 310 may also generate a user warning 309 in response to the strain snapshots. FIG. 6 however also illustrates the interaction of the processing unit 310 with a power control unit 312 and a clock control unit 314 of the apparatus. The power control 312 is arranged to control the power state of each component of the apparatus (comprising both the processing unit 310 and the generically illustrated components 316) through the distribution of power control signals to each. Thus on the basis of the pattern of strain snapshots stored in the strain history storage, processing unit 310 may cause the power control unit 312 to put either the entire system or certain components thereof into a power-off mode (except for wake-up logic) to avoid a predicted period of strain or stress and performing critical tasks. Such defensive mitigating operation can extend the lifetime of the apparatus. In a similar manner the processing unit 310 may control the clock control 314, which distributes clock signals to the components of the apparatus, in order to dynamically control their clock speeds, such that components may be run faster or slower depending on the current strain mode.

Figure 7:
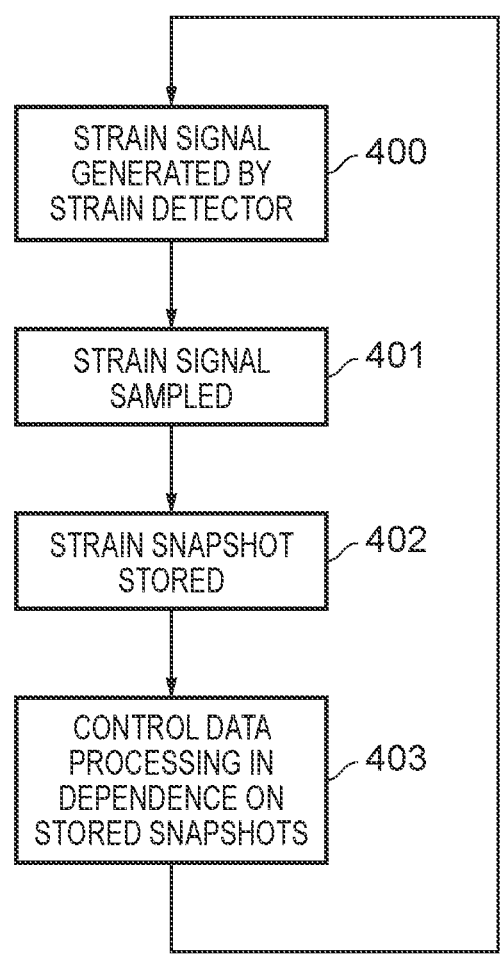
FIG. 7 is a flow diagram schematically illustrating a sequence of steps which are taken in the method of some embodiments.

FIG. 7 is a flow diagram showing a sequence of steps which are taken according to the method of some embodiments, for example when operating one of the apparatus embodiments described above with reference to the preceding figures. The flow can be considered to begin at step 400, where a strain signal is generated by a strain detector. This strain signal is then sampled at step 401 and on the basis thereof a strain snapshot is stored at step 402. At step 403 data processing is controlled in dependence on a sequence of such stored strain snapshots. The flow is shown to return from step 403 to step 400 since this is a continuously ongoing process.

Figure 8:
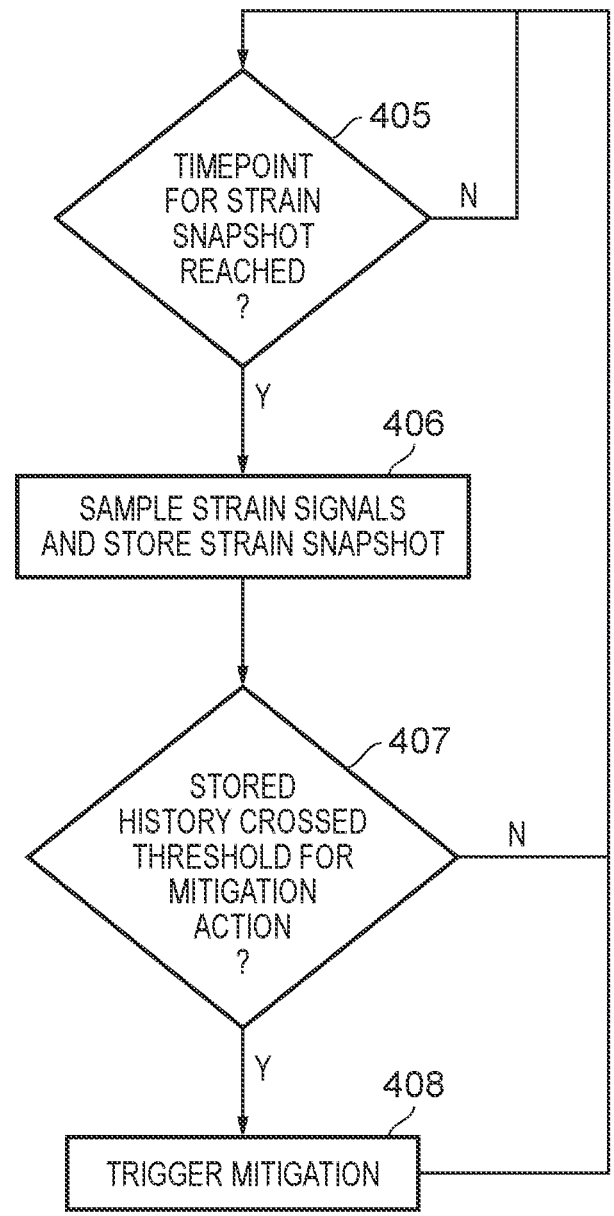
FIG. 8 is a flow diagram schematically illustrating a sequence of steps which are taken in the method of some embodiments.

FIG. 8 is a flow diagram showing a sequence of steps which are taken according to the method of some embodiments, for example when operating one of the apparatus embodiments described above with reference to the preceding figures. The flow can be considered to begin at step 405, where it is determined if a time point for a strain snapshot to be recorded has been reached. If it has not then the flow loops upon itself here until this point is reached. Then (when such a snapshot time point is reached) at step 406 the strain signals from multiple strain detectors are sampled and a derivative strain snapshot is stored. It is then determined at step 407 if the history of strain snapshots stored has crossed a threshold (i.e. one or more required criteria are satisfied) for mitigation action to be taken. If this is not the case then the flow simply returns to step 405. However when this is the case then at step 408 mitigation action is triggered (which may for example be one of the actions, such as a variation in power mode or clock speed, or the generation of a signal to a user as described above). The flow then returns to step 405.

In brief overall summary, apparatuses and methods of operating apparatuses are disclosed. An apparatus comprises a flexible substrate and circuitry fabricated on the flexible substrate to perform data processing. At least one strain detector generates a strain signal which is dependent on a flexing state of the strain detector on the flexible substrate. A strain history control unit samples the at least one strain signal from the at least one strain detector at a plurality of time points and records a strain snapshot at each time point comprising data dependent on the at least one strain signal from the at least one strain detector. The data processing performed by the circuitry is dependent on the plurality of strain snapshots recorded.

In the present application, the words "configured to . . . " are used to mean that an element of an apparatus has a configuration able to carry out the defined operation. In this context, a "configuration" means an arrangement or manner of interconnection of hardware or software. For example, the apparatus may have dedicated hardware which provides the defined operation, or a processor or other processing device may be programmed to perform the function. "Configured to" does not imply that the apparatus element needs to be changed in any way in order to provide the defined operation.

Although illustrative embodiments have been described in detail herein with reference to the accompanying drawings, it is to be understood that the invention is not limited to those precise embodiments, and that various changes, additions and modifications can be effected therein by one skilled in the art without departing from the scope of the invention as defined by the appended claims. For example, various combinations of the features of the dependent claims could be made with the features of the independent claims without departing from the scope of the present invention.

What is claimed is:

1. An apparatus comprising:
   a flexible substrate; and
   circuitry fabricated on the flexible substrate to perform data processing, wherein the circuitry comprises:
      at least one strain detector arranged to generate a strain signal which is dependent on a flexing state of the strain detector on the flexible substrate; and
      a strain history control unit arranged to sample the at least one strain signal from the at least one strain detector at a plurality of time points and to record a strain snapshot at each time point comprising data dependent on the at least one strain signal from the at least one strain detector,
   wherein the apparatus is configured to modify data processing operations performed by the circuitry in dependence on the plurality of strain snapshots recorded.

2. The apparatus as claimed in claim 1, wherein the data dependent on the at least one strain signal from the at least one strain detector recorded by the strain history control unit comprises a strain indication dependent on the at least one strain signal, wherein the strain indication is taken from a finite set of discrete strain states, and wherein the finite set of discrete strain states comprise an unstrained state and at least one strained state.

3. The apparatus as claimed in claim 2, wherein the at least one strained state comprises an in-tension state and an in-compression state.

4. The apparatus as claimed in claim 2, wherein the strain history control unit is arranged to record the strain indication for each strain detector.

5. The apparatus as claimed in claim 2, wherein the strain history control unit is arranged to record the strain indication as a summary strain indication for all strain detectors.

6. The apparatus as claimed in claim 5, wherein the strain history control unit is arranged to determine the summary strain indication by majority vote of strain indications of each strain detector.

7. The apparatus as claimed in claim 1, wherein the strain history control unit is arranged to record the strain snapshot at each time point further comprising location information of the at least one strain detector.

8. The apparatus as claimed in claim 1, further comprising a strain history storage, wherein the strain history control unit is arranged to record the strain snapshot at each time point in the strain history storage.

9. The apparatus as claimed in claim 8, wherein the circuitry comprises a data processing unit, and wherein the data processing unit has access to the strain history storage and wherein the data processing unit is arranged to control the data processing performed by the circuitry in dependence on the plurality of strain snapshots recorded.

10. The apparatus as claimed in claim 8, wherein the circuitry comprises a strain predictor, wherein the strain predictor has access to the strain history storage and wherein the strain predictor is arranged to generate a strain prediction indicative of a predicted period of flexing of the flexible substrate in dependence on the plurality of strain snapshots recorded.

11. The apparatus as claimed in claim 10, wherein the circuitry is responsive to the strain prediction indicative of the predicted period of flexing to enter a reduced activity mode for the predicted period, wherein the reduced activity mode comprises at least one of:
   at least some components of the circuitry being in a low power state;
   at least some components of the circuitry being provided with a reduced frequency clock signal; and
   at least some components of the circuitry being powered off.

12. The apparatus as claimed in claim 1, wherein the data processing performed by the circuitry comprises generation of an ageing prediction for the apparatus, wherein the ageing prediction is dependent on the plurality of strain snapshots recorded.

13. The apparatus as claimed in claim 1, wherein the at least one strain detector is arranged to operate at a clock speed defined when the flexing state of the at least one strain detector on the flexible substrate is an in-compression state.

14. The apparatus as claimed in claim 1, wherein the at least one strain detector is arranged to operate at a clock speed defined when the flexing state of the at least one strain detector on the flexible substrate is comprises an in-tension state.

15. The apparatus as claimed in claim 1, wherein the circuitry comprises a plurality of strain detectors randomly distributed across the flexible substrate.

16. The apparatus as claimed in claim 1, wherein the circuitry comprises a plurality of strain detectors distributed in a regular pattern across the flexible substrate.

17. The apparatus as claimed in claim 1, wherein the circuitry comprises a plurality of strain detectors distributed across the flexible substrate, wherein each strain detector is positioned in association with a component of the circuitry.

18. The apparatus as claimed in claim 1, wherein the circuitry fabricated on the flexible substrate comprises a flexible system-on-chip, wherein the strain signal generated by the strain detector on the flexible substrate is indicative of a flexing state of the flexible system-on-chip.

19. A method of operating an apparatus, wherein the apparatus comprises a flexible substrate and circuitry fabricated on the flexible substrate to perform data processing, the circuitry comprising at least one strain detector, the method comprising:
  generating a strain signal in the at least one strain detector which is dependent on a flexing state of the strain detector on the flexible substrate;
  sampling the at least one strain signal from the at least one strain detector at a plurality of time points;
  recording a strain snapshot at each time point comprising data dependent on the at least one strain signal from the at least one strain detector; and
  modifying data processing operations performed by the circuitry in dependence on the plurality of strain snapshots recorded.

20. A apparatus comprising:
  a flexible substrate;
  circuitry fabricated on the flexible substrate to perform data processing;
  at least one means for generating a strain signal which is dependent on a flexing state of the flexible substrate;
  means for sampling the strain signal from the at least one strain detector at a plurality of time points;
  means for recording a strain snapshot at each time point comprising data dependent on the at least one strain signal; and
  means for modifying data processing operations performed by the circuitry in dependence on the plurality of strain snapshots recorded.

* * * * *